United States Patent [19]

Atwell et al.

[11] Patent Number: 4,590,277
[45] Date of Patent: May 20, 1986

[54] ACRIDINECARBOXAMIDE COMPOUNDS

[75] Inventors: Graham J. Atwell; Bruce C. Baguley; William A. Denny; Gordon W. Rewcastle, all of Auckland, New Zealand

[73] Assignee: Development Finance Corporation of New Zealand, New Zealand

[21] Appl. No.: 506,335

[22] Filed: Jun. 21, 1983

[30] Foreign Application Priority Data

Jun. 25, 1982 [NZ] New Zealand ................ 201084

[51] Int. Cl.⁴ .................. C07D 219/10; C07D 219/04; A61K 31/47
[52] U.S. Cl. .................................... 546/105; 546/102; 546/103; 546/104; 546/106; 514/908
[58] Field of Search ............... 546/102, 103, 104, 105, 546/106, 107; 424/257; 514/297

[56] References Cited

U.S. PATENT DOCUMENTS

| | | | |
|---|---|---|---|
| 3,686,180 | 8/1972 | Sutton | 546/102 |
| 4,366,318 | 12/1982 | Cain et al. | 546/106 |
| 4,472,582 | 9/1984 | Cain et al. | 546/106 |
| 4,479,000 | 10/1984 | Rewcastle et al. | 546/23 |

FOREIGN PATENT DOCUMENTS

| | | | |
|---|---|---|---|
| 0025705 | 3/1981 | European Pat. Off. | 424/257 |
| 0027388 | 11/1969 | Japan | 546/103 |

OTHER PUBLICATIONS

Cain et al., J. Med. Chem., vol. 19, No. 9, pp. 1124-1129 (1976).
Barker et al., J. Org. Chem., vol. 46, pp. 2455-2465 (1981).
Cain et al., J. Med. Chem., 80 20(8), pp. 987-996 (1977).
Denny et al., J. Med. Chem., 22(12), pp. 1453-1460 (1979).
Baguley et al., J. Med. Chem., 24(5), pp. 520-532 (1981).
Matsumura, Chemical Abstracts, vol. 32, 3405 4-7 (1938).
Albert et al., Chemical Abstracts, vol. 41, 458c (1947).
Stapleton et al., Chemical Abstracts, vol. 49, 8968b (1955).
Fujihira et al., Chemical Abstracts, vol. 74, 139208v (1971).
Burdeska, K. et al., Helv. Chim. Acta, 55(6), 1948-14 1958 (1972) [Chem. Abst. 78, p. 86, 17591b (1973)].
Chem. Substance Index 1972-1976, p. 775 CS, col. 1, lines 5-7.

Primary Examiner—Donald G. Daus
Assistant Examiner—Diana G. Rivers
Attorney, Agent, or Firm—Pennie & Edmonds

[57] ABSTRACT

4-Carboxamidoacridine compounds represented by the general formula (I),

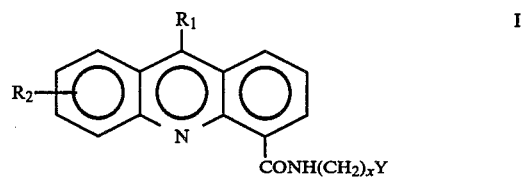

where
$R_1$ represents H, $CH_3$ or $NHR_3$, where $R_3$ is H, $COCH_3$, $SO_2CH_3$, $COPh$, $SO_2Ph$ or lower alkyl optionally substituted with hydroxyl and/or amino functions;
$R_2$ represents H or up to two of the groups $CH_3$, $OCH_3$, halogen, $CF_3$, $NO_2$, $NH_2$, $NHCOCH_3$, and $NHCOOCH_3$ placed at positions 1-3 or 5-8;
Y represents $C(NH)NH_2$, $NHC(NH)NH_2$, or $NR_4R_5$, where each of $R_4$ and $R_5$ is H or lower alkyl optionally substituted with hydroxyl and/or amino functions; and
x is from 2 to 6, and the acid addition salts thereof, possess antibacterial and antitumor properties.

7 Claims, No Drawings

ACRIDINECARBOXAMIDE COMPOUNDS

BACKGROUND TO THE INVENTION

Various amino- and alkylamino-acridines have previously been evaluated as antitumour agents (M. R. Lewis and P. P. Goland, *J. Amer. Med. Sci.*, 215, 282 (1948)), and some have been found to be active in vivo against Ehrlich ascites tumours (N. Schummenfelder, W. Wessel, E. Nessel, *Z. Krebsforsch.*, 63, 129 (1959)). Local clinical cytostatic effects have also been observed with mepacrine (J. Ultmann, A. Gellhorn, K. Osnos and E. Hirschburg, *Cancer*, 16, 283 (1963)). A variety of 9-alkylaminoacridines bearing an additional alkylating function off the sidechain are active in some animal tumour systems (R. M. Peck, R. K. Preston and H. J. Creech, *J. Amer. Chem. Soc.*, 81, 3984 (1959)). A large number of 9-dialkylaminoalkylamino acridines have been evaluated for antitumour activity (see C. Radzikowski, A. Ledochowski, M. Hrabowska, et al., *Arch. Immunol. Ther. Exp.*, 17, 86 & 99 (1969), A. Hrabowska, A. Ledochowski and K. Onoszko, *Arch. Immunol. Ther. Exp.*, 25, 253 (1977), and J. Gieldanowski, Z. Wieczorek et al., *Arch. Immunol. Ther. Exp.*, 28, 755 (1980)), but only those compounds bearing a 1-$NO_2$ group have shown convincing activity. A compound of this class, nitracrine, has been used in Poland for some years as a clinical antitumour agent (M. Warwas, B. Narezewska, W. Dobryszycka, *Arch. Immunol. Ther. Exp.*, 25, 235 (1977)).

N-alkylated acridones have long been known to have convulsant properties (S. E. Mayer and J. E. Bain, *J. Pharmacol. Exp. Ther.*, 118, 17 (1956)) and a related 1-$NO_2$ analogue has been reported to have antitumour activity (A. Pelczarska, S. H. Kowalczyk-Bronisz et al., *Arch. Immunol. Ther. Exp.*, 22, 823, 843 (1974)). Analogues of amsacrine bearing in the 4-position a $CONH(CH_2)_xN(CH_3)_2$ substituent, in which x is 2 or 3, are active antitumour agents in vivo (W. A. Denny et al., *J. Med. Chem.*, 25, 276 (1982)). However, there have been no reports of acridine compounds bearing sidechains off the 4-position having been prepared or evaluated for antitumour activity.

We have now found a novel class of acridinecarboxamide compounds which have antibacterial and antitumour properties.

SUMMARY OF THE INVENTION

It is the object of the present invention to provide novel 4-carboxamidoacridine derivatives having antibacterial and antitumour properties and methods for preparing these compounds.

It is a further object of the present invention to provide novel compounds useful as intermediates in the preparation of the acridine derivatives of the invention.

DESCRIPTION OF THE INVENTION

The novel 4-carboxamidoacridine derivatives of the present invention are the compounds represented by the general formula (I),

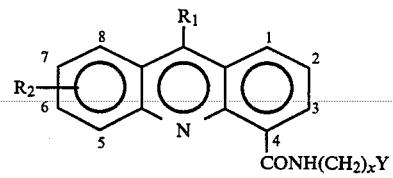

where
$R_1$ represents H, $CH_3$ or $NHR_3$, where $R_3$ is H, $COCH_3$, $SO_2CH_3$, $COPh$, $SO_2Ph$ or lower alkyl optionally substituted with hydroxyl and/or amino functions;

$R_2$ represents H or up to two of the groups $CH_3$, $OCH_3$, halogen, $CF_3$, $NO_2$, $NH_2$, $NHCOCH_3$, and $NHCOOCH_3$ placed at positions 1-3 or 5-8;

Y represents $C(NH)NH_2$, $NHC(NH)NH_2$, or $NR_4R_5$, where each of $R_4$ and $R_5$ is H or lower alkyl optionally substituted with hydroxyl and/or amino functions; and x is from 2 to 6,
and the acid addition salts thereof.

When $R_3$, $R_4$ or $R_5$ represent lower alkyl, the group may contain from 1 to 4 carbon atoms.

A preferred subclass of these compounds of formula (I) are those where $R_1$ represents $NH_2$, $R_2$ represents up to two of 1-, 5-, 6-, 7- or 8-$NO_2$, 5-or 6-$CH_3$, and 5-Cl, Y represents $NHC(NH)NH_2$, $N(CH_3)_2$, or $NHCH_2CH_2OH$ and x is 2.

Another preferred subclass of these compounds of formula (I) has the same values for $R_2$, Y and x but $R_1$ represents H.

Four specific compounds of formula (I) are those in which, (a) $R_1$ and $R_2$ represent H, Y represents $N(CH_3)_2$ and x is 2;

(b) $R_1$ represents $NH_2$, $R_2$ represents H, Y represents $N(CH_3)_2$ and x is 2;

(c) $R_1$ represents $NH_2$, $R_2$ represents 6-$NO_2$, Y represents $N(CH_3)_2$ and x is 2; and (d) $R_1$ represents $NH_2$, $R_2$ represents 5-$CH_3$, Y represents $N(CH_3)_2$ and x is 2.

Other specific compounds of formula (I) are listed in Tables I and II hereinafter.

The compounds of formula (I) form pharmaceutically acceptable addition salts with both organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic, and the like.

The compounds of general formula (I) and the acid addition salts thereof may be prepared by a process which comprises coupling a substituted acridine of the general formula (II),

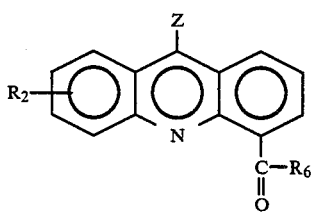

where $R_2$ is as defined as above, Z represents H, $CH_3$, or any suitable leaving group (e.g. methoxy, phenoxy, alkylthio or halogen, but preferably chloro) and $R_6$ represents Cl, Br or $OC_6H_4$-p-$NO_2$, with a primary alkyl amine of the general formula (III), $$NH_2(CH_2)_xY \qquad \text{III}$$

where x and Y are as defined above, and, when Z is a leaving group, converting the resultant coupled product to a compound of general formula (I) where $R_1$ represents $NHR_3$ and $R_3$ is as defined above, and, if desired, converting a compound of formula (I) into an acid addition salt thereof.

The coupling reaction is desirably performed in an anhydrous solvent (e.g. chloroform, dimethylsulphoxide or N-methylpyrrolidone, but preferably dichloromethane or dimethylformamide) buffered with a tertiary amine, preferably triethylamine. The reaction is conveniently performed at temperatures in the range from 0° C. to 50° C., with the preferred temperature being 20° C.

In the case of Z representing Cl in formula (II), further treatment of the resulting coupled products with anhydrous ammonia or suitable amine of the general formula $R_3NH_2$ in phenol or cresol provides the compounds of formula (I) where $R_1$ represents $NHR_3$. Alternatively, treating the resulting coupled products where Z=Cl with neat phenol or cresol provides corresponding compounds where Z=$OC_6H_5$ or $OC_6H_4CH_3$ and $R_6$ is $NH(CH_2)_xY$, where x and Y are defined as for formula (I). These compounds can be isolated, but are usually treated in situ with anhydrous ammonia or amine $R_3NH_2$ to provide the desired compounds of general formula (I).

The acid addition salts of the compounds of formula (I) are prepared by contacting the free base form with an equivalent amount of the desired acid in the conventional manner. The free base forms may be regenerated by treating the salt form with a base. For example, dilute aqueous base solutions may be utilized. Dilute aqueous potassium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for the purposes of the invention.

The primary alkyl amines of the general formula (III) are known compounds and are commercially available or preparable by methods described in the literature.

Examples of such compounds include N,N-dimethyl-1,2-ethanediamine (N,N-dimethylethylenediamine), N,N-diethyl-1,2-ethanediamine, N,N-dimethyl-1,3-propanediamine, N,N-dimethyl-1,4-butanediamine, N,N-dimethyl-1,5-pentanediamine, N-(2-hydroxymethyl)-1,2-ethanediamine (2-(2-aminoethylamino)-ethanol), N-methyl-N-(2-hydroxyethyl)-1,2-ethanediamine, 2-aminoethylguanidine $NH_2(CH_2)_2NHC(NH)NH_2$, and 3-aminopropionamidine $NH_2(CH_2)_2C(NH)NH_2$. The two last-mentioned compounds may be prepared according to P. L. Barker, P. L. Gendler, and H. Rapoport, *J. Org. Chem.*, 46, 2455 (1981).

The amines of the general formula $R_3NH_2$ are also known compounds, and are commercially available or preparable by methods described in the literature. Examples of such compounds where $R_3$ is lower alkyl optionally substituted with hydroxyl and/or amino functions include methylamine, ethylamine, 2-hydroxethylamine, 2,3-dihydroxy propylamine, and N,N-dimethyl-1,2-ethanediamine (N,N-dimethylethylenediamine).

The 9-substituted acridines of formula (II) are novel compounds useful as intermediates in the preparation of the compounds of formula (I), and accordingly the present invention also provides the compounds represented by the general formula (II),

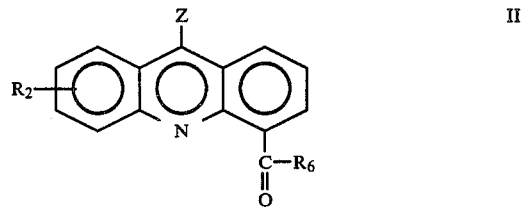

where $R_2$ is defined as for formula (I), Z represents H, $CH_3$, or any suitable leaving group (e.g. methoxy, phenoxy, alkylthio or halogen but preferably chloro) and $R_6$ represents Cl, Br or $OC_6H_4$-p-$NO_2$.

The 9-substituted acridines of general formula (II) where Z represents H or halogen may be prepared by the process outlined in Scheme I, and this general process also forms part of the present invention. In Scheme I, $R_2$ is as defined for formula (I), and $R_6$ is as defined for formula (II).

Scheme I

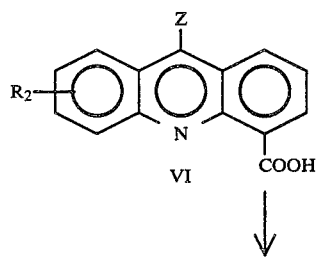

-continued
Scheme I

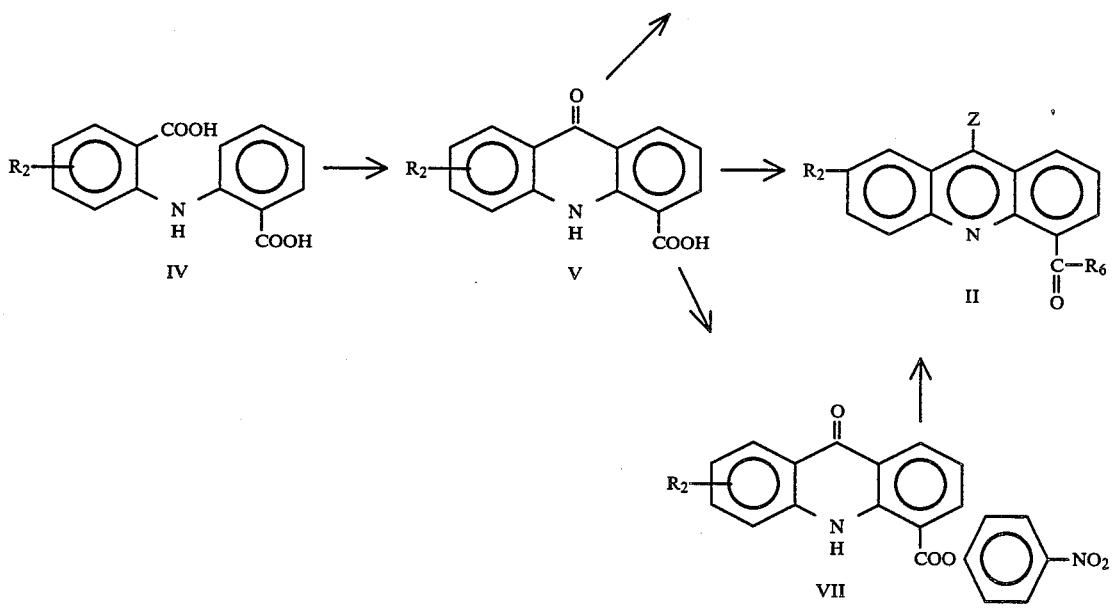

The diphenylamine diacids (IV) are formed by the Jourdan-Ullmann reaction between suitably substituted 2-halobenzoic acids and anthranilic acids in high yield (see B. F. Cain, G. J. Atwell and W. A. Denny, *J. Med. Chem.*, 20, 987 (1977) and G. W. Rewcastle, G. J. Atwell, B. C. Baguley and W. A. Denny, U.S. patent application Ser. No. 409,594, filed Aug. 19, 1982. The resulting diphenylamine diacids (IV) are cyclodehydrated with mineral acids or their derivatives (e.g. $H_2SO_4$, polyphosphoric acid or polyphosphate ester) to form carboxyacridanones, from which the desired 4-carboxy isomers (V) are obtained if necessary by separation from co-occurring isomers. Such separations can readily be achieved by taking advantage of the differential solubilities of the different isomers, both as free acids and acid salts.

Alternatively, the formation of unwanted isomers in the cyclodehydration reaction can be avoided by the process outlined in Scheme II, and this general process also forms part of the present invention. In Scheme II, $R_2$ is as defined for formula (I), and $R_7$ represents a lower alkyl group, i.e. containing from 1 to 4 carbon atoms, preferably methyl or t-butyl, and X is a halogen, preferably Cl or Br, or phenyl-iodonium.

Scheme II

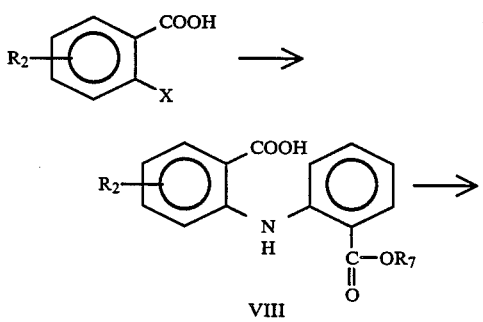

-continued
Scheme II

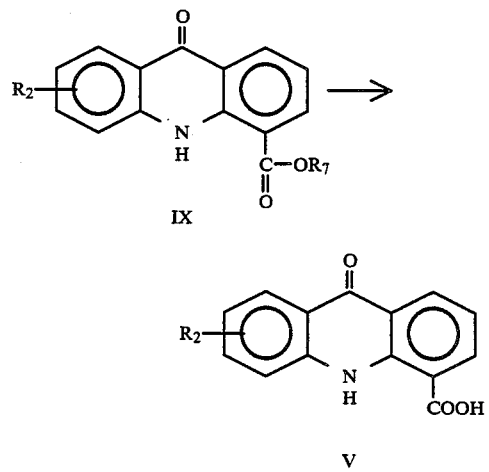

The diphenylamine esters (VIII) are formed via a novel modification of the Jourdan-Ullmann reaction, in which a suitable organic base (e.g. tri-n-butylamine, N-ethylmorpholine or diisopropylethylamine) is used as both solvent and acid acceptor, thus preventing hydrolysis of the ester group. A soluble form of copper catalyst such as copper (II) acetate is used. Ring closure of the diphenylamine esters (VIII) is effected without concomitant hydrolysis of the ester function by using polyphosphate ester (PPE) as reagent. Subsequent acid- or base-catalysed hydrolysis of the acridone esters (IX) gives the desired products (V).

The acridone esters represented by the general formula (IX),

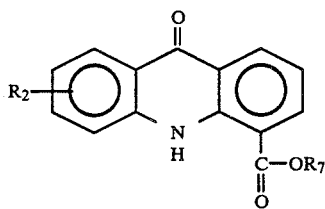

IX where $R_2$ is as defined for formula (I) and $R_7$ represents a lower alkyl group, preferably methyl or t-butyl, are novel compounds useful as intermediates in the preparation of the compounds of formula (I), and they accordingly form part of the present invention.

An alternative preparation of the 4-carboxy compounds of formula (V) is outlined in Scheme III, and this general process also forms part of the present invention. In Scheme III, $R_2$ is as defined for formula (I) and X represents halogen but preferably iodo.

Scheme III

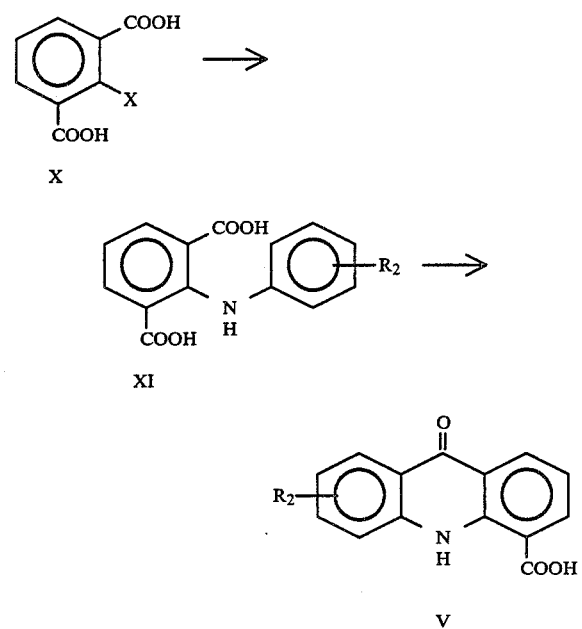

Reaction of the halodiacid with the appropriately substituted amine is carried out in an anhydrous solvent such as N-methylpyrrolidone or dimethylsulphoxide (DMSO), but preferably dimethylformamide (DMF), in the presence of acid acceptors such as $K_2CO_3$ and organic bases (preferably N-ethylmorpholine) and Cu powder to give the N-substituted diacid (XI). These are conveniently isolated by diluting the reaction mixture with water and extracting with suitable organic solvents, preferably ethyl acetate. The resulting diphenylamine diacids are cyclodehydrated with mineral acids or their derivatives as described above to form carboxyacridanones, from which the desired 4-carboxyacridanones (V) are obtained if necessary by separation from co-occurring isomers as described above.

Reduction of the substituted 4-carboxyacridanones (V) to substituted 4-carboxyacridines (VI, Z=H), in Scheme I, can be achieved by direct treatment with Al/Hg amalgam (A. Albert and E. Ritchie, J. Soc. Chem Ind., 60, 120 (1941), or by formation of the tosylhydrazide adduct (VI, Z=NHNHSO$_2$C$_6$H$_4$CH$_3$) via the corresponding 9-chlorocompound, (VI, Z=Cl), and subsequent basecatalyzed decomposition of the adduct (A. Albert and A. Royer, J. Chem. Soc., 1148, (1949)). Reaction of the 4-carboxyacridanones (V) with tris(4-nitrophenyl)phosphite in pyridine gives the 4-nitrophenylester derivatives (VII) (B. F. Cain, G. J. Atwell and W. A. Denny, J. Med. Chem., 20, 987 (1977). Similar reaction of the 4-carboxyacridines (VI, Z=H) with tris (4-nitrophenyl)phosphite in pyridine gives the compounds of general formula (II) where Z is H and $R_6$ is OC$_6$H$_4$-p-NO$_2$.

Compounds of general formula (V) can be activated by reaction with a suitable halogen reagent (e.g. PCl$_5$, POCl$_3$, but preferably SOCl$_2$) and a trace of DMF as catalyst to provide compounds of formula (II) where Z is Cl and $R_6$ is Cl. Similar activation of compounds of general formula (VI) provides compounds of formula (II) where Z is H and $R_6$ is Cl. Similar activation of compounds of general formula (VII) provides compounds of formula (II) where Z is Cl and $R_6$ is OC$_6$H$_4$-p-NO$_2$.

Similar activation of compounds of general formula (V), (VI) or (VII) with POBr$_3$ or preferably SOBr$_2$ provides compounds of formula (II) where Z is Br and $R_6$ is Br, Z is H and $R_6$ is Br, or Z is Br and $R_6$ is OC$_6$H$_4$-p-NO$_2$.

These compounds of general formula (II) where Z is H, Cl or Br can then be reacted with amines of general formula (III) in anhydrous solvents (e.g. CHCl$_3$, DMSO or N-methylpyrrolidone, but preferably CH$_2$Cl$_2$ or DMF) buffered with a tertiary amine (preferably triethylamine).

The method of preparation when an amine of formula (III) is reacted with a compound of formula (II) where $R_6$ is OC$_6$H$_4$-p-NO$_2$ is the preferred method when the sidechain component (III) contains, in addition to the primary amine, other secondary amine or hydroxylated amine functions Y.

The compounds of general formula (II) where Z is alkylthio can be prepared by the methods cited in E. F. Elslager et al., J. Med. Chem., 14, 782–788 (1971), and the resultant products from the coupling reaction with amines of general formula (III) can be converted to compounds of formula (I) where $R_1$ is NHR$_3$ by the methods also cited therein.

The compounds of general formula (II) where Z is methoxy or phenoxy can be prepared by the methods given in Albert, "The Acridines", Second Edition, Edward Arnold Ltd, London (1966).

The 9-substituted acridines of general formula (II) wherein Z represents CH$_3$ may be prepared by the process outlined in Scheme IV, and this general process also forms part of the present invention. In Scheme IV, X represents halogen but preferably bromo, $R_2$ and $R_6$ are as defined for formula (II) and $R_8$ is as defined below.

Scheme IV

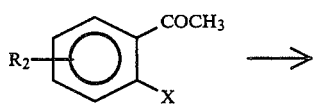

-continued
Scheme IV

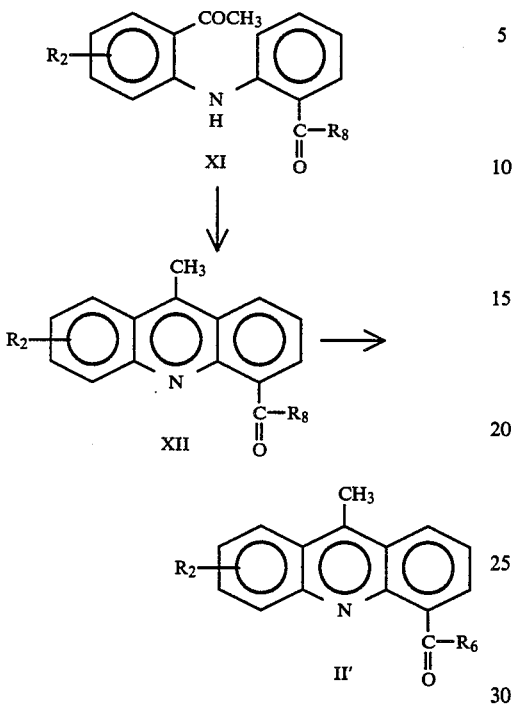

Reaction of suitably substituted 2-haloacetophenones with anthranilic acid in the presence of 1 mole of acid acceptor (preferably potassium carbonate) and a catalytic amount of copper gives the diphenylamine products (XI), where $R_8$ is OH. Reaction of the ketoacids (XI; $R_8$=OH) with a suitable lower alcohol (preferably ethanol) using 1 mole of diethyl phosphorocyanidate (DEPC) or other suitable ester-forming reagents and 1 mole of acid acceptor, preferably triethylamine, gives compounds (XI, $R_8$=OCH$_2$CH$_3$). Cyclodehydration, for example using 5% $H_2SO_4$ in refluxing acetic acid, provides compounds (XII; $R_8$=OCH$_2$CH$_3$), which can be hydrolyzed in dilute ethanolic sodium hydroxide to the acid (XII; $R_8$=OH). Activation of these compounds with a suitable halogen reagent (preferably SOCl$_2$ or SOBr$_2$) as detailed above provides compounds of general formula (II) where Z is CH$_3$ and $R_6$ is Cl or Br. Reaction of the acid (XII; $R_8$=OH) with tris(4-nitrophenyl)phosphite in pyridine gives the 4-nitrophenylester derivatives (II';$R_6$=OC$_6$H$_4$-p-NO$_2$) (B. F. Cain, G. J. Atwell and W. A. Denny, *J. Med. Chem.*, 20, 987 (1977).

The compounds of general formula (II) where Z is CH$_3$ and $R_6$ is Cl, Br or OC$_6$H$_4$-p-NO$_2$ are then coupled with suitable primary amines of general formula (III) in anhydrous solvent (e.g. CHCl$_3$, DMSO or N-methylpyrrolidone, but preferably CH$_2$Cl$_2$ or DMF) buffered with a tertiary amine (preferably triethylamine) to provide compounds of general formula (I) where $R_1$ is CH$_3$.

An alternative and preferred process for the preparation of compounds of general formula (I) where $R_1$ is CH$_3$ and $R_2$ is defined as for formula (I) is outlined in Scheme V, and this is also a process of the present invention. In Scheme V, X represents halogen but preferably bromo, $R_2$ and Y are as defined for formula (I) and $R_8$ is as defined below.

Scheme V

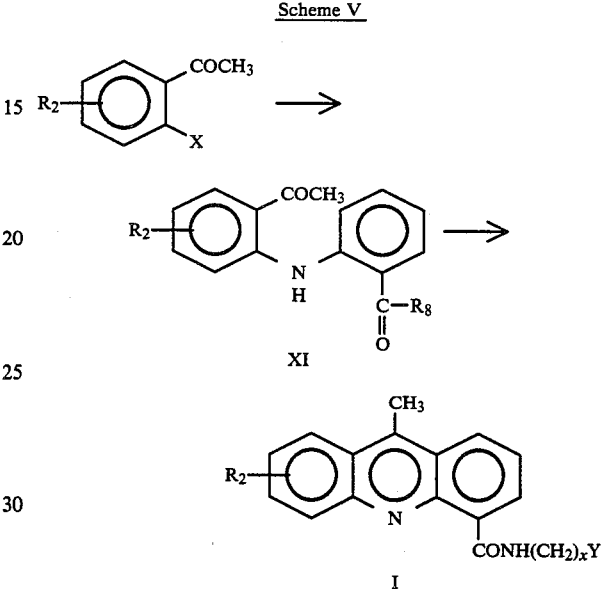

Reaction of suitably substituted 2-haloacetophenones with anthranilic acid in the presence of 1 mole of acid acceptor (preferably potassium carbonate) and a catalytic amount of copper gives the diphenylamine products (XI), where $R_8$ is OH. These compounds can be coupled with a primary alkyl amine of general formula (III) in anhydrous solvents (e.g. N-methylpyrrolidone or N-methyl acetamide but preferably DMF) using 1 mole of diethyl phosphorocyanidate or other suitable amide-forming reagent and 1 mole of an acid acceptor, preferably anhydrous triethylamine to give compounds (XI), where $R_8$ is NH(CH$_2$)$_x$Y. Cyclodehydration of these compounds, for example using 5% $H_2SO_4$ in refluxing acetic acid, gives the required compounds of general formula (I), where $R_1$ is CH$_3$.

The following Tables I and II set out physical data for 24 compounds within the general formula (I), representative of it, and preparable by the processes of the invention. In Table I the following terms and abbreviations are used:

MP=melting point of the reported acid addition salt in °C.

Rm=a measure of the compound's lipophilic-hydrophilic balance from reversed phase partition chromatography. Rm is linearly related to partition coefficients obtained in the 1-octanol/water system.

TABLE I

| No | $R_1$ | $R_2$ | x | Y | Mp | Formula | Rm |
|---|---|---|---|---|---|---|---|
| 1 | H | H | 2 | N(CH$_3$)$_2$ | 195–197 | C$_{18}$H$_{19}$N$_3$O.2HCl | −0.20 |
| 2 | CH$_3$ | H | 2 | N(CH$_3$)$_2$ | 178–180 | C$_{19}$H$_{21}$N$_3$O.2HCl | −0.30 |
| 3 | NHCH$_3$ | H | 2 | N(CH$_3$)$_2$ | 231–233 | C$_{19}$H$_{22}$N$_4$O.2HCl | −1.11 |
| 4 | NH$_2$ | H | 2 | N(CH$_3$)$_2$ | 292–293 | C$_{18}$H$_{20}$N$_4$O.2HCl ½H$_2$O | −1.11 |
| 5 | NH$_2$ | H | 3 | N(CH$_3$)$_2$ | 290–292 | C$_{19}$H$_{22}$N$_4$O.2HCl | −0.93 |
| 6 | NH$_2$ | H | 2 | NH(CH$_2$)$_2$OH | 292–293 | C$_{18}$H$_{20}$N$_4$O$_2$.2HCl | −1.06 |

TABLE I-continued

| No | $R_1$ | $R_2$ | x | Y | Mp | Formula | Rm |
|---|---|---|---|---|---|---|---|
| 7 | $NH_2$ | H | 2 | $N(CH_2CH_3)_2$ | 283–285 | $C_{20}H_{24}N_4O.2HCl$ | −0.67 |
| 8 | $NH_2$ | H | 2 | $NH_2$ | 344–345 | $C_{16}H_{16}N_4O.2HCl$ | −1.18 |
| 9 | $NH_2$ | 2-$NO_2$ | 2 | $N(CH_3)_2$ | >360 | $C_{18}H_{19}N_5O_3.2HCl$ | |
| 10 | $NH_2$ | 2-$NH_2$ | 2 | $N(CH_3)_2$ | >360 | $C_{18}H_{21}N_5O.2HCl.H_2O$ | |
| 11 | $NH_2$ | 5-$NO_2$ | 2 | $N(CH_3)_2$ | >360 | $C_{18}H_{19}N_5O_3.2HCl$ | |
| 12 | $NH_2$ | 5-$NH_2$ | 2 | $N(CH_3)_2$ | 326–329 | $C_{18}H_{21}N_5O.2HCl.H_2O$ | |
| 13 | $NH_2$ | 5-$CH_3$ | 2 | $N(CH_3)_2$ | 321–323 | $C_{19}H_{22}N_4O.2HCl$ | −1.02 |
| 14 | $NH_2$ | 5-$OCH_3$ | 2 | $N(CH_3)_2$ | >360 | $C_{19}H_{22}N_4O_2.2HCl$ | −1.06 |
| 15 | $NH_2$ | 5-Cl | 2 | $N(CH_3)_2$ | 311–312 | $C_{18}H_{19}ClN_4O.2HCl$ | |
| 16 | $NH_2$ | 6-$NO_2$ | 2 | $N(CH_3)_2$ | >360 | $C_{18}H_{19}N_5O_3.2HCl$ | |
| 17 | $NH_2$ | 6-$NH_2$ | 2 | $N(CH_3)_2$ | >360 | $C_{18}H_{21}N_5O.2HCl$ | |
| 18 | $NH_2$ | 6-$CH_3$ | 2 | $N(CH_3)_2$ | 326–328 | $C_{19}H_{22}N_4O.2HCl$ | −0.82 |
| 19 | $NH_2$ | 6-$OCH_3$ | 2 | $N(CH_3)_2$ | 256–258 | $C_{19}H_{22}N_4O_2.2HCl$ | |
| 20 | $NH_2$ | 7-$NO_2$ | 2 | $N(CH_3)_2$ | 316–318 | $C_{18}H_{19}N_5O_3.2HCl$ | −1.29 |
| 21 | $NH_2$ | 7-$NH_2$ | 2 | $N(CH_3)_2$ | 324–326 | $C_{18}H_{21}N_5O.3HCl$ | −1.64 |
| 22 | $NH_2$ | 7-$CH_3$ | 2 | $N(CH_3)_2$ | 316–319 | $C_{19}H_{22}N_4O.2HCl$ | |
| 23 | $NH_2$ | 7-$OCH_3$ | 2 | $N(CH_3)_2$ | 290–292 | $C_{19}H_{22}N_4O_2.2HCl \tfrac{1}{2}H_2O$ | |
| 24 | $NH_2$ | 7-Cl | 2 | $N(CH_3)_2$ | 310–311 | $C_{18}H_{19}ClN_4O.2HCl$ | |

TABLE II

Elemental analyses for the compounds of Table I

| | | Found | | | | Calculated | | | |
|---|---|---|---|---|---|---|---|---|---|
| No | Formula | C | H | N | Cl | C | H | N | Cl |
| 1 | $C_{18}H_{19}N_3O.2HCl$ | 59.1 | 5.9 | 11.7 | 19.0 | 59.0 | 5.8 | 11.5 | 19.4 |
| 2 | $C_{19}H_{21}N_3O.2HCl$ | 60.3 | 6.0 | 11.0 | 18.5 | 60.0 | 6.1 | 11.1 | 18.6 |
| 3 | $C_{19}H_{22}N_4O.2HCl$ | 57.6 | 6.4 | 14.1 | 18.5 | 57.7 | 6.1 | 14.2 | 17.9 |
| 4 | $C_{18}H_{20}N_4O.2HCl \tfrac{1}{2}H_2O$ | 55.7 | 6.4 | 14.5 | 18.0 | 55.4 | 5.9 | 14.4 | 18.2 |
| 5 | $C_{19}H_{22}N_4O.2HCl$ | 58.1 | 6.3 | 14.6 | | 57.7 | 6.1 | 14.2 | |
| 6 | $C_{18}H_{20}N_4O_2.2HCl$ | 54.2 | 5.7 | 14.0 | 17.6 | 54.4 | 5.6 | 14.1 | 17.8 |
| 7 | $C_{20}H_{24}N_4O.2HCl$ | 59.1 | 6.5 | 13.6 | 17.1 | 58.7 | 6.4 | 13.7 | 17.3 |
| 8 | $C_{16}H_{16}N_4O.2HCl$ | 54.5 | 5.1 | 16.0 | 19.8 | 54.4 | 5.1 | 15.9 | 20.1 |
| 9 | $C_{18}H_{19}N_5O_3.2HCl$ | 50.5 | 4.8 | 16.4 | 16.8 | 50.7 | 5.0 | 16.4 | 16.6 |
| 10 | $C_{18}H_{21}N_5O.2HCl.H_2O$ | 52.0 | 5.9 | 16.7 | | 52.2 | 6.1 | 16.9 | |
| 11 | $C_{18}H_{19}N_5O_3.2HCl$ | 50.5 | 5.2 | 16.5 | 16.6 | 50.7 | 5.0 | 16.4 | 16.6 |
| 12 | $C_{18}H_{21}N_5O.2HCl.H_2O$ | 52.6 | 6.0 | 17.1 | | 52.2 | 6.1 | 16.9 | |
| 13 | $C_{19}H_{22}N_4O.2HCl$ | 58.2 | 6.2 | 14.2 | 17.9 | 57.7 | 6.1 | 14.2 | 17.9 |
| 14 | $C_{19}H_{22}N_4O_2.2HCl$ | 55.5 | 6.4 | 13.2 | 16.5 | 55.5 | 5.9 | 13.6 | 17.2 |
| 15 | $C_{18}H_{19}ClN_4O.2HCl$ | 52.0 | 5.0 | 13.4 | 25.2 | 52.0 | 5.1 | 13.5 | 25.6 |
| 16 | $C_{18}H_{19}N_5O_3.2HCl$ | 50.6 | 5.2 | 16.4 | 16.5 | 50.7 | 5.0 | 16.4 | 16.6 |
| 17 | $C_{18}H_{21}N_5O.2HCl$ | 54.6 | 5.6 | 17.8 | 17.8 | 54.5 | 5.9 | 17.7 | 17.9 |
| 18 | $C_{19}H_{22}N_4O.2HCl$ | 57.8 | 6.1 | 14.3 | 17.9 | 57.7 | 6.1 | 14.2 | 17.9 |
| 19 | $C_{19}H_{22}N_4O_2.2HCl$ | 55.1 | 6.1 | 13.8 | 17.7 | 55.4 | 5.9 | 13.6 | 17.3 |
| 20 | $C_{18}H_{19}N_5O_3.2HCl$ | 51.0 | 4.9 | 16.3 | 16.1 | 50.7 | 5.0 | 16.4 | 16.6 |
| 21 | $C_{18}H_{21}N_5O.3HCl$ | 50.0 | 5.5 | 16.4 | 24.2 | 49.9 | 5.6 | 16.2 | 24.6 |
| 22 | $C_{19}H_{22}N_4O.2HCl$ | 57.4 | 5.9 | 14.0 | 17.8 | 57.7 | 6.1 | 14.2 | 17.9 |
| 23 | $C_{19}H_{22}N_4O_2.2HCl \tfrac{1}{2}H_2O$ | 54.4 | 6.2 | 13.1 | 16.5 | 54.3 | 6.0 | 13.3 | 16.9 |
| 24 | $C_{18}H_{19}ClN_4O.2HCl$ | 52.5 | 4.7 | 13.5 | 25.4 | 52.0 | 5.1 | 13.5 | 25.6 |

The following Examples illustrate the preparation of compounds of the general formula (I):

EXAMPLE A

Preparation of compound 4 of Table I by the method of Scheme I

N-(2-Carboxyphenyl)anthranilic Acid (IV, $R_2$=H)

A mixture of 2-chlorobenzoic acid (100 g), anthranilic acid (90 g), anhydrous powered $K_2CO_3$ (135 g), Cu/CuO (2 g) and 2-ethoxyethanol (200 ml) was heated with swirling on the steam bath until gas evolution ceased and then stirred at 145° for a further 2½ hours. The thick reaction mixture was diluted with water, acidified (HCl) and then the crude product was collected and washed well with hot water. This was dissolved in hot dilute aqueous $Na_2CO_3$ treated liberally with charcoal-celite and filtered through a celite pad. The hot filtrate was diluted with half the volume of EtOH and then slowly acidified (HCl). The pale yellow product which separated was collected when still warm, washed well with hot water, benzene and dried, providing material (84% yield) of sufficient purity for use in the next step (lit, m.p. 295° dec.).

9(10H)Acridone-4-carboxyic Acid (V, $R_2$=H)

A mixture of the preceding diphenylamine diacid (80 g) and conc. $H_2SO_4$ (250 ml) was heated at 100° C. for 4 hours, then cooled, poured into ice-water and the precipitated solid collected and washed well with water. This was dissolved in dilute aqueous NaOH and following filtration was diluted with an equal volume of EtOH and then acidified with glacial acetic acid (this left any sulfonated impurities in solution). The acridone acid which slowly crystallized from the hot solution was collected after thorough cooling, washed with EtOH, water, EtOH again and dried providing pure material in 83% yield m.p. 342°–343° dec.

9-Chloroacridine-4-carbonyl chloride (II, $R_2$=H, Z=Cl; $R_6$=Cl)

A suspension of the preceding acridone acid (20 g) in $SOCl_2$ (60 ml) containing DMF (2 drops) was heated gently under reflux with stirring until homogeneous and then for a further 45 min. The solution was evaporated to dryness in vacuo, below 40° C., and residual traces of SOCl₂ were removed by addition of dry benzene and complete re-evaporation of all solvents to give the crude product as a yellow powder.

N-]2-(dimethylamino)ethyl] 9-chloroacridine-4-carboxamide (II, R$_2$=H, Z=Cl, R$_6$=NH(CH$_2$)$_2$ N(CH$_3$)$_2$.

The above carbonyl chloride was cooled to −5° and to this was added in one portion an ice-cold solution of N,N-dimethylethylenediamine (36.5 ml) in dry dichloromethane (200 ml). After stirring at 30° C. until homogeneous the reaction solution was left for a further 15 min and then shaken with dilute aq. Na₂CO₃. The organic layer was washed with dilute aq. Na₂CO₃ (2x), aq. NaCl solution and then dried (Na₂SO₄). Evaporation of the solvent left an oil which slowly solidified. This was extracted with hot dry benzene-petroleum ether (1:5), treated with charcoal-celite and filtered quickly through a hot celite pad. Crystalline material rapidly separated and addition of further petroleum ether completed precipitation of the product. The yellow solid was collected, washed with petroleum ether and dried providing material 19.5 g (71% yield) indicated by TLC to contain only trace quantities of the corresponding acridone and this product was stored over KOH and used without further purification.

Compound 4 of Table 1

The above compound (II; R$_2$=H, Z=Cl, R$_6$=NH(CH$_2$)$_2$N(CH$_3$)$_2$ (4.0 g) was dissolved in dry phenol (12.8 g) and heated slowly to 50° C., to provide a solution of the phenoxy compound (II; R$_2$=H, Z=OC$_6$H$_5$), R$_6$=NH(CH$_2$)$_2$ NH(CH$_3$)$_2$) in excess phenol. A stream of dry ammonia was passed into the solution while the temperature was raised from 50° C. to 115° C. Addition of ammonia was continued for 15 min, after which the mixture was cooled and diluted with excess 40% aqueous NaOH. Prolonged cooling gave a solid that was crystallized from aqueous EtOH and then EtOAc. The resulting pure base was converted to the dihydrochloride salt by dissolving in MeOH, treating with 12N HCl (2.2 equivalents) and precipitating with EtOAc. Crystallization from MeOH/EtOAc gave hygroscopic yellow prisms of the pure dihydrochloride of compound 4, m.p. 304°–305° C. (72% yield).

Minor modifications of the procedure of Example A, employing appropriately substituted 2-chlorobenzoic acids and/or appropriate amine components, were used to prepare compounds 3,5,7,8,9-15 and 18 of Table I. Separation of isomers after ring closure was sometimes required.

EXAMPLE B

Preparation of compound 1 of Table 1 by the method of Scheme I

4-Carboxyacridine (VI; Z=H, R$_2$=H)

4-Carboxyacridanone (V; R$_2$=H)(5 g) and NaOH (1g; 1.1 equivalent) were dissolved in water (100 ml). Al foil (3 g; amalgamated by dipping each piece into a solution of 15 g of aercuric chloride in 100 ml of water for 5 min immediately before use) was added in pieces to the stirred, boiling solution of carboxyacridanone over 30 min. After a further 30 min reflux, the hot solution was filtered and acidified with cHCl. FeCl₃ (12 g) was added, and the mixture was heated until clear (an initial heavy precipitate redissolves) and for a further 10 mins. The mixture was basified with 2N NaOH, filtered from Fe(OH)₃, and the pH adjusted to 5, when a precipitate formed. This was collected, washed with water and extracted with boiling EtOH (400 ml). The filtrate was concentrated to 30 ml and cooled well, yielding 4-carboxyacridine (2.2 g, 47%), m.p. 202°–204° C.

Compound 1 of Table I

4-Carboxyacridine (1.1 g, 5.6 mM) was refluxed in SOCl₂ (10 ml) and a drop of DMF for 1 h, and the volatiles were evaporated. Dry benzene (20 ml) was added and evaporated to remove residual traces of SOCl₂, and the resulting solid was dissolved in dry DMF (20 ml) containing N,N-dimethylethylenediamine (1.25 g, 3 equivalents). The mixture was kept at 20° C. for 2 h and the volatiles were evaporated at 40° C. The resulting gum was extracted with boiling diisopropyl ether, and this solution was concentrated and diluted with petroleum ether to give the free base as yellow needles (0.85 g, 61%). The free base was dissolved in MeOH and dry HCl gas added to pH2. Dilution with EtOAc gave the dihydrochloride as yellow crystals (87%), m.p. 195°–197° C.

EXAMPLE C

The preparation of compounds 20 and 21 of Table I by the methods of Scheme I and Scheme II.

N-(2-methoxycarbonylphenyl)-5-nitroanthranilic acid (VIII, R$_2$=7-N$_2$, R$_7$ =CH$_3$)

A mixture of 2-chloro-5-nitrobenzoic acid (7 g, 35 mM), methyl anthranilate (6.3 g, 45 mM), and cupric acetate (6.3 g, 35 mM) in bis-isopropylethylamine (10 ml) and N-methylpyrrolidone (5 ml) was stirred and heated at 150° for 2 h under N₂. The cooled solution was diluted with water and acidified with 2N HCl. The gummy precipitate was collected by decantation and triturated with a small amount of cold MeOH to give a yellow solid. This was collected and washed with cold MeOH to give the desired diphenylamine ester (VIII; R$_2$=7-N$_2$, R$_7$=CH$_3$) (2.6 g, 24%). Crystallization from EtoAc gave yellow needles, m.p. 228°–229° C.

Methyl 7-nitro-acridanone-4-carboxylate (IX, R$_2$=7-NO$_2$, R$_7$=CH$_3$)

The above diphenylamine ester (2.0 g) was heated at 100° C. for 1 h with polyphosphate ester (10 g). The cooled mixture was diluted with water and basified with Na₂CO₃ to give the acridone ester, which was collected and crystallized from EtOH as yellow needles, m.p. 310°–312° C. (1.7 g, 91% yield).

7-Nitro-4-carboxyacridanone (V, R$_2$=7-NO$_2$)

The above acridone ester (2.0 g) was heated in 92% H$_2$SO$_4$ (50 ml) for 7 h at 100° C. The cooled mixture was poured into water and the precipitate collected and extracted with aqueous Na$_2$CO$_3$. The extract was filtered and acidified with 2N HCl to provide pure product (1.72 g, 90%), which was recrystallized from DMF as a yellow powder, m.p. about 375° C.

7-Nitro-4-carboxyacridanone (V; R$_2$=7-NO$_2$) (by direct nitration)

A stirred solution of 4-carboxyacridanone (10.0 g) in c.H$_2$SO$_4$ (50 ml) was treated portionwise at below 5° C. with powdered KNO$_3$ (4.6 g), then stirred for 30 min at 20° C. and poured into ice water. The precipitate was collected, washed, dried and crystallized from DMF/MeOH and then DMF to give pure product of m.p. about 375° C. (65% yield).

The product was identical (assessed by TLC) to the compound obtained above by polyphosphate ester ring closure of N-(2-methoxycarboxyphenyl)-5-nitroanthranilic acid and subsequent acid hydrolysis of the methyl ester function.

Compound 20 of Table I

The above 7-nitro-4-carboxyacridanone was converted to 7-nitro-9-chloroacridine-4-carbonyl chloride (II, Z=Cl, R$_2$=7-NO$_2$, R$_3$=Cl), and treated with N,N-dimethylethylenediamine followed by dry ammonia in phenol by the methods outlined in Example A above to give N-(2-dimethylaminoethyl)-9-amino-7-nitroacridine-4-carboxamide dihydrochloride (compound 20 of Table I), m.p. 316°-318° C.

Compound 21 of Table I

The above nitro compound was reduced using Fe powder and HCl in 65% aqueous EtOH. Basification with 2N NaOH gave the crude product, which was converted to the trihydrochloride with 12N HCl in MeOH/EtOAc. Two recrystallizations from MeOH-/EtOAc gave pure product, m.p. 324°-326° C.

EXAMPLE D

Preparation of compound 6 of Table I by the method of Scheme I

6-p-Nitrophenyl acridanone-4-carboxylate. (VII; R$_2$=H)

Pure, finely-powered acridanone-4-carboxylic acid (19.8 g, 83 mM) and p-nitrophenol (22.2 g, 160 mM) were suspended in pyridine (200 ml). The mixture was stirred vigorously at 60° C. while PCl$_3$ (4.4 ml; 53 mM) was added dropwise. The mixture was immediately heated to 100° C. until homogeneous. On cooling product separated, and after 1 h the reaction was cooled well and the precipitate collected and washed well with acetone. Recrystallization from DMF gave pure compound (74% yield), m.p. 280°-281° C.

p-Nitrophenyl 9-chloroacridine-4-carboxylate (II; Z=Cl, R$_2$=H, R$_6$=OC$_6$H$_4$NO$_2$)

The above compound (2.02 g, 5.6 mM) was refluxed gently in SOCl$_2$ (6 ml) and a drop of DMF for 1 h. The volatiles were evaporated, dry benzene was added, and the volatiles evaporated again to remove all traces of HCl and SOCl$_2$. The residue was dissolved in CH$_2$Cl$_2$, cooled to 0° C., and icecold 10% KHCO$_3$ (20 ml) was added. The organic layer was separated, dried, and concentrated to small volume to provide the product as yellow needles (80% yield), m.p. 194°-196° C.

Compound 6 of Table I

4-Nitrophenyl 9-chloroacridine-4-carboxylate (0.01M) was added in one portion to an ice-cooled stirred solution of 2-(2-aminoethylamino)-ethanol (0.012M) and triethylamine (0.011M) in anhydrous dichloromethane (20 ml). The mixture was stirred until homogeneous, and then for a further 10 min. Dry phenol (11 g) was then added to the solution and anhydrous ammonia was passed in while the temperature was raised to 115° C. After contact with ammonia at this temperature for a further 10 min the mixture was cooled and excess 5N aqueous NaOH added. The resulting solid was dissolved in 1N aqueous HCl and this solution was slowly neutralised with 1N aqueous NH$_4$OH, precipitating a quantity of material that was removed by filtration and discarded. Treatment of the filtrate with excess aqueous NaOH gave crude material which was recycled through the above purification process. The resulting free base was crystallized from MeOH-H$_2$O. Crystallisation of the dihydrochloride salt from MeOH-EtOAc then provided pure product, m.p. 292°-293° C. dec.

EXAMPLE E

Preparation of compound 2 of Table I by the method of Scheme V

2-(N-2-Methylcarbonylphenyl)aminobenzoic acid (XI; R$_2$=H, R$_8$=OH)

A mixture of 2-chloroacetophenone (20 g, 0.18 mol), anthranilic acid (37 g, 0.27 mol), dry K$_2$CO$_3$ (37 g. 0.27 mol), Cu powder (0.1 g), and CuCl (0.1 g) suspended in 50 ml dimethoxyethane was stirred under reflux for 20 h and cooled. The mixture was extracted with dilute aqueous NaOH, the solution was clarified with charcoalcelite, filtered, and acidified to give 7.4 g (16%) of 2-(N-2-methylcarbonylphenyl)aminobenzoic acid, (XI; R$_2$=H, R$_8$=OH) m.p. 280°-283° decomp.(EtOH).

N-(2-Dimethylaminoethyl)-2-(N-2-methylcarbonylphenyl) aminobenzamide (XI; R$_2$=H, R$_8$=NH(CH$_2$)$_2$ N(CH$_3$)$_2$)

A solution of the above keto-acid in dry DMF (20 ml) was treated with 2.3 g (1.2 equivalents) of diethyl phosphorocyanidate (DEPC), and an excess of N,N-dimethylethylenediamine (2 g) was added dropwise. After being warmed on a waterbath for 30 min the reaction mixture was basified with K$_2$CO$_3$ (aq) and the solvent was removed under vacuum. The residue was extracted with ethyl acetate, and after being washed (H$_2$O,brine) and dried (Na$_2$SO$_4$) the solvent was removed to give crude N-(2-dimethylaminoethyl)-2-(N-2-methylcarbonylphenyl) aminobenzamide, (XI; R$_2$=H, R$_8$=NH(CH$_2$)$_2$ N(CH$_3$)$_2$) as an oil.

Compound 2 of Table I

The above oily product was dissolved in 25 ml of a mixture of 100 parts HOAc and 5 parts H$_2$SO$_4$. After heating under reflux for 1 h the HOAc was removed under vacuum and the residue was dissolved in water. The aqueous fraction was extracted with CH$_2$Cl$_2$, basified with aqueous NaOH and extracted with EtOAc. The EtOAc layer was washed with water and saturated brine, dried and evaporated to provide N-(2-dimethylaminoethyl)-9-methylacridine-4-carboxamide (2.1 g, 60%) as an oil. This was dissolved in MeOH-EtOAc and treated with dry HCl gas to provide compound 2 of Table I as a crystalline dihydrochloride salt, m.p. 178°–180° C. (recrystallized from EtOH).

Alternative Preparation of Compound 2 of Table I by the method of Scheme IV

Ethyl 9-methylacridine-4-carboxylate (XII; $R_2=H$, $R_8=OEt$).

To a solution of 1.2 g (4.7 mmol) of 2-(N-2-methylcarbonylphenyl) aminobenzoic acid in 5 ml dry DMF was added 1.15 g DEPC (1.5 equivalents), ethanol (1 ml) and $Et_3N$ (1.4 g, 3 equivalents) and the mixture was heated on a water bath for 1 h. Since the reaction was incomplete a further equivalent of each reagent was added and the mixture was heated for a further 1 h. The solvent was removed under vacuum, and the residue was basified with $KHCO_3$(aq) and extracted into EtOAc. After washing and drying ($Na_2SO_4$) the solvent was removed to give the crude ethyl ester (XI: $R_2=H$, $R_8=OEt$) which was dissolved in 15 ml of a mixture of HOAc (100 parts) and $H_2SO_4$ (5 parts). After heating under reflux for 1 h the HOAc was removed under vacuum and the residue was basified with dil $KHCO_3$ solution, and extracted with EtOAc. The organic layer was washed with dilute aqueous methanesulphonic acid and discarded, and after being basified with dil. $KHCO_3$ solution the aqueous layer was extracted with EtOAc to give 0.31 g of ethyl 9-methylacridine-4-carboxylate (XII; $R_2=H$, $R_8=OEt$) (23%) as an oil.

N-(2-Dimethylaminoethyl)-9-methylacridine-4-carboxamide. (Compound 2 of Table I)

The ethyl ester from above (1 mmol) was treated with refluxing 1N NaOH in 20 ml 60% aqueous ethanol for 1 h; the solution was neutralized by the dropwise addition of conc. HCl and the solvent was removed under vacuum. The crude acid (XII; $R_2=H$, $R_8=OH$) was then treated with refluxing $SOCl_2$ for 30 min, and after removal of the solvent the product acid chloride (XII; $R_2=H$, $R_8=Cl$) was dissolved in dry $CH_2Cl_2$. The solution was cooled in ice and an excess of N,N-dimethylethylenediamine was then added slowly. The solution was then washed well with water to remove excess amine and after being dried ($Na_2SO_4$) the solvent was removed to give N-(2-dimethylaminoethyl)-9-methylacridine 4-carboxamide (0.24 g, 78%) as an oil. This oil was converted to the crystalline hydrochloride salt (compound 2 of Table I), m.p. 178°–180° decomp (EtOH).

EXAMPLE F

Preparation of Compound 16 of Table I by the method of Scheme II

5-Nitrodiphenyliodonium-2-carboxylate

2-Iodo-4-nitrobenzoic acid (17.5 g, 0.06 mol) (W.C. Agosta, Tet. Lett., 1965, 2681) was dissolved in 60 ml conc $H_2SO_4$ and the solution was cooled to 0° C. Potassium persulphate (31.2 g, 0.116 mol) was added in portions with stirring over 40 min, and after a further 60 min at <10° C. 55 ml of benzene was added. The stirred viscous mixture was then allowed to warm slowly to room temperature and left overnight. The reaction mixture was then poured onto ice, and the white precipitate was filtered off and suspended in a stirred solution of 200 ml 5N NaOH. After being filtered off and washed several times with water the solid was dried by azeotroping with benzene. Yield 20.1 g, 91%. The product was insoluble in all of the normal solvent systems but has some solubility in DMF.

N-[2-(Methoxycarbonyl)phenyl]-4-nitro-anthranilic acid (VIII)

Crude 5-Nitrodiphenyliodonium-2-carboxylate (42 g, 0.114 mol) was suspended in 500 ml of DMF containing 34 g methyl anthranilate and 1.0 g $Cu(OAc)_2$, and the mixture was heated on a waterbath for 2 days when all of the solid had dissolved. The dark red-brown solution was diluted firstly with 50 ml of conc $NH_3$, and then with 2 L of water and the oily insolubles were removed by washing twice with dichloromethane. Acidification with dilute HCl then gave the nitro ester acid, 31.3 g, 86%, which was recrystallized from EtOAc as red needles, m.p. 243°–245° C.

Methyl 6-nitro-9(10H)-acridanone-4-carboxylate (IX)

The above half ester (1.0 g, 3.2 mM) was heated with polyphosphate ester at 100° C. for 1 h. The cooled product was diluted with water and basified to pH 9. The insoluble product was collected and crystallized from ethanol as yellow prisms: m.p. 252°–253° C.

6-Nitro-4-carboxy-9(10H)-acridanone (V)

The above acridone ester (1.5 g, 5.0 mM) was heated in sulphuric acid (20 ml, 92% v/v) for 7 h at 100° C. The cooled mixture was diluted with water, and the product collected and washed. Trituration with 2N aq $Na_2CO_3$ followed by removal of insoluble products and acidification of the filtrate gave the acid (1.29 g, 90% yield). A sample was crystallized from a large volume of EtOH, : m.p. 375° C. Attempted ester hydrolysis under basic conditions gave impure, deeply coloured products.

Compound 16 of Table I

The above 4-carboxyacridanone was converted, via the 9-chloro-4-carbonyl chloride to compound 16 of Table I, using the methods given in Example A.

EXAMPLE G

Preparation of compound 23 of Table I by the method of Scheme III 2-(4-Methoxyphenylamino)-1,3-benzenedicarboxylic acid (XI)

A mixture of 10 g 2-iodoisophthalic acid (34 mmol), 8.3 g p-anisidine (70 mmol), 0.5 g CuCl, 0.5 g $Cu(OAc)_2$, 10 ml N-ethylmorpholine and 25 ml DMF was heated with stirring at 125° C. for 2 h under nitrogen and cooled. The reaction mixture was then diluted with 100 ml of dil HCl and extracted with EtOAc. The organic layer was extracted with dil NaOH solution and discarded. Acidification of the aqueous layer with dil HCl gave a precipitate of the methoxy-diacid, 8.64 g, 88% m.p. 226°–228° C. (EtOAc).

7-Methoxy-4-carboxy-9(10H)-acridamine (V)

The above diacid (4.3 g, 30 mM) was treated with polyphosphoric acid (30 g) for 4 h at 130° C. The cooled melt was dissolved in water and the pH was adjusted to 7.5 with aqueous NaOH to precipitate the crude acridone acid.

Compound 23 of Table I

The above crude acridanone acid was treated as outlined in Example A to provide compound 23 of Table I.

The procedure of Example G was also used with appropriate choice of starting materials to prepare compounds 19, 22 and 24 of Table I.

The compounds of general formula (I) show broad-spectrum antibacterial activity. Specifically, compound 4 is active against the bacteria *Aerobacter aerogenes, Alcaligenes viscolatis, Escherichia coli, Bacillus subtilis, Sarcina lutea, Micrococcus lysodeikticus, Neisseria catarrhalis, Staphylococcus aureus, Xanthomonas phaseoli* and *Streptococcus faecalis.*

The compounds of general formula (1), and particularly the examples listed in Tables I and II, have antitumour activity in in vivo and for in vitro test systems, as shown by the data of Table III. This Table gives biological data for compounds 1-24, whose physical data has been given in Tables I and II. The abbreviations given in Table III are:

P388 in vivo—Tumour P388 cells were obtained as frozen stocks from Mason Research Inc., U.S.A. and passaged intraperitoneally according to standard methods (*Cancer Chemother. Rep.* 3, Part 3, page 9, 1972) in DBA-2 mice of either sex. Groups of six Fl hybrid mice (DBA-2 male x C57 B1 female, g weight 20±1 g) were injected intraperitoneally with $10^6$ cells on day 0.

O.D.—optimal drug dose, in milligrams per kilogram, administered as a solution in 0.1 ml of 30% v/v ethyl alcohol in water on days 1, 5 and 9 after tumour inoculation. The drug is administered as a soluble acid addition salt.

ILS—percentage increase in life span of treated animals over that of groups of control animals injected with tumour alone. The average survival of control mice was 11 days. Values of ILS greater than 20% are considered statistically significant.

L1210 in vitro—The culture methods used are described in detail elsewhere (B. C. Baguley and R. Nash, *Europ. J. Cancer,* 17, 671-679 (1981)). Acceptable reproducibility of data depends critically upon the maintenance of optimal culture conditions. L1210 cells were initially obtained from Dr I. Wodinsky, Arthur D. Little Inc., Boston, U.S.A., under the auspices of the National Cancer Institute.

$ID_{50}$ —the nanomolar concentration of drug which when added to cultures of murine L1210 leukaemic cells over a period of 70 hours, reduces the resultant counted number of leukaemia cells by 50% (B. C. Baguley and R. Nash, *Europ. J. Cancer,* 17, 671-679 (1981)). Values below 1000 nM are considered significant.

Y. implies a significant value of drug activity at the stated dose.

N. implies no or not statistically significant activity.

TABLE III

| | Biological data for the compounds of Table I | | | |
|---|---|---|---|---|
| | L1210 in vitro | P388 in vivo | | |
| No. | $ID_{50}$ | OD | ILS | Active |
| 1 | 105 | 66 | 91 | Y |
| 2 | 66 | 45 | 14 | N |
| 3 | 15 | 5.9 | 53 | Y |
| 4 | 15 | 4.5 | 98 | Y |
| 5 | 157 | 20 | 0 | N |
| 6 | 77 | 20 | 80 | Y |
| 7 | 5.5 | 5.9 | 70 | Y |
| 8 | 414 | 20 | 71 | Y |
| 9 | 319 | 8.9 | 25 | Y |
| 10 | 162 | 30 | 28 | Y |
| 11 | 1.3 | 0.8 | 39 | Y |
| 12 | 18 | 8.9 | 58 | Y |
| 13 | 0.33 | 2.6 | 107 | Y |
| 14 | 4.3 | 3.9 | 81 | Y |
| 15 | 2.9 | 2.6 | 81 | Y |
| 16 | 0.05 | 2.6 | 23 | Y |
| 17 | 35 | 8.9 | 58 | Y |
| 18 | 55 | 2.6 | 20 | N |
| 19 | 151 | 8.9 | 17 | N |
| 20 | 104 | 20 | 34 | Y |
| 21 | 48 | 20 | 80 | Y |
| 22 | 605 | 13.3 | 0 | N |
| 23 | 518 | 13.3 | 4 | N |
| 24 | 722 | 13.3 | 8 | N |

It is clear from the data of Table III that the acridine carboxamides of general formula I are active antitumour agents, giving significant levels of life extension when tested against the P388 leukaemia system when given by intraperitoneal injection, and/or significant inhibition of cultured L1210 leukaemia cells in vitro. The compounds also show antitumour activity when given by oral and intravenous routes. In addition to high cytotoxicity towards cultured L1210 leukaemia cells, they are active in a number of cultured tumour cell lines, including those originating from human breast and colon tumours.

These compounds are thus indicated for use as antitumour agents, and the present invention also provides pharmaceutical compositions having antitumour activity and comprising at least one compound of the general formula (I), or a pharmaceutically acceptable acid addition salt thereof, and one or more pharmaceutically acceptable carriers or diluents.

The present invention further provides a method for treating tumours and in particular cancers in a patient which comprises administering to the patient an antitumour effective amount of a compound of formula (I) or a pharmaceutically acceptable acid addition salt thereof.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% and about 60% of the weight of the unit. The amount of active compound in such therapeutically useful compositions is such that a suitable dosage will be obtained. Preferred compositions or preparations according to the present invention are prepared so that an oral dosage unit form contains between about 5 and about 200 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmaceutically acceptable salt can be prepared in water suitably mixed with a surfactant such a hydroxpropylcellulose. Dispersons can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils. The proper fluidity can be maintained, for example, by the use of a coating such a lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungl agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 0.1 to about 400 mg. with from about one to about 30 mg being preferred. Expressed in proportions, the active compound is generally present in from about 0.1 to about 400 mg/ml of carrier. In the case of compositions containing supplementary active ingredients, the dosages are determined by reference to the usual dose and manner of administration of the said ingredients.

What is claimed is:

1. A compound represented by by the general formula (I),

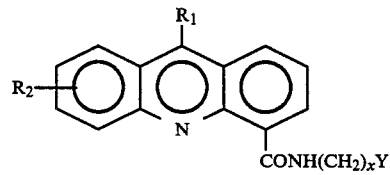

where
$R_1$ represents H or $NHR_3$, where $R_3$ is H, $COCH_3$, $SO_2CH_3$, $COPh$, $SO_2Ph$ or lower alkyl optionally substituted with hydroxyl and/or amino groups;
$R_2$ represents H or up to two of the groups $CH_3$, $OCH_3$, halogen, $CF_3$, $NO_2$, $NH_2$, $NHCOCH_3$, and $NHCOOCH_3$ placed at positions 1-3 or 5-8;
Y represents $C(NH)NH_2$, $NHC(NH)NH_2$, or $NR_4R_5$, where each of $R_4$ and $R_5$ is H or lower alkyl optionally substituted with hydroxyl and/or amino groups; and
x is from 2 to 6,
or an acid addition salt thereof.

2. A compound according to claim 1 where $R_1$ represents $NH_2$, $R_2$ represents up to two of 1-, 5-, 6-, 7-, or 8-$NO_2$, 5- or 6-$CH_3$, and 5-Cl, Y represents $NHC(NH)NH_2$, $N(CH_3)_2$ or $NHCH_2CH_2OH$ and x is 2.

3. A compound according to claim 1 where $R_1$ represents H, $R_2$ represents up to two of 1-, 5-, 6-, 7-, or 8-$NO_2$, 5- or 6-$CH_3$, and 5-Cl, Y represents $NHC(NH)NH_2$, $N(CH_3)_2$ or $NHCH_2CH_2OH$ and x is 2.

4. A compound according to claim 1 in which $R_1$ and $R_2$ represent H, Y represents $N(CH_3)_2$ and x is 2.

5. A compound represented by the formula

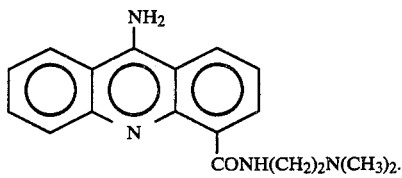

6. A compound represented by the formula

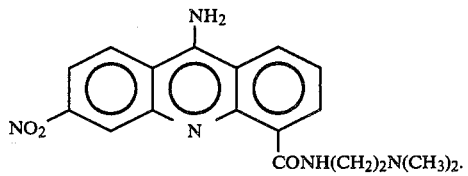

7. A compound represented by the formula

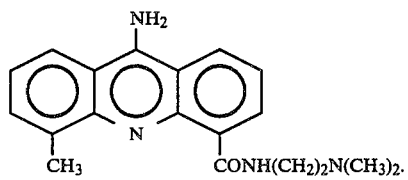

* * * * *